United States Patent
Ritzberger et al.

(10) Patent No.: US 9,321,674 B2
(45) Date of Patent: Apr. 26, 2016

(54) LITHIUM SILICATE GLASS CERAMIC AND GLASS WITH TRANSITION METAL OXIDE

(71) Applicant: Ivoclar Vivadent AG, Schaan (LI)

(72) Inventors: Christian Ritzberger, Grabs (CH); Wolfram Höland, Schaan (LI); Marcel Schweiger, Chur (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/275,099

(22) Filed: May 12, 2014

(65) Prior Publication Data

US 2014/0335473 A1    Nov. 13, 2014

Related U.S. Application Data

(63) Continuation of application No. 13/079,063, filed on Apr. 4, 2011, now Pat. No. 8,759,237.

(30) Foreign Application Priority Data

Apr. 16, 2010   (EP) ..................................... 10160222
Jul. 7, 2010    (EP) ..................................... 10168792

(51) Int. Cl.

| | |
|---|---|
| C03C 10/12 | (2006.01) |
| C03C 10/00 | (2006.01) |
| A61K 6/02 | (2006.01) |
| A61K 6/027 | (2006.01) |
| C03C 3/095 | (2006.01) |
| C03C 4/00 | (2006.01) |
| C03C 14/00 | (2006.01) |
| A61C 5/10 | (2006.01) |
| A61C 13/00 | (2006.01) |
| A61K 6/06 | (2006.01) |
| C03B 32/02 | (2006.01) |
| C09K 11/02 | (2006.01) |

(52) U.S. Cl.
CPC .............. *C03C 10/0027* (2013.01); *A61C 5/10* (2013.01); *A61C 13/0003* (2013.01); *A61C 13/0004* (2013.01); *A61C 13/0006* (2013.01); *A61C 13/0022* (2013.01); *A61K 6/023* (2013.01); *A61K 6/024* (2013.01); *A61K 6/025* (2013.01); *A61K 6/0215* (2013.01); *A61K 6/0235* (2013.01); *A61K 6/0245* (2013.01); *A61K 6/0255* (2013.01); *A61K 6/0273* (2013.01); *A61K 6/0612* (2013.01); *C03B 32/02* (2013.01); *C03C 3/095* (2013.01); *C03C 4/0021* (2013.01); *C03C 14/00* (2013.01); *C09K 11/025* (2013.01); *C03C 2204/00* (2013.01); *Y10T 29/49567* (2015.01)

(58) Field of Classification Search
CPC ...... C03C 3/097; C03C 3/095; C03C 10/0009
USPC ................. 501/5, 6, 7, 63, 64, 68, 69, 70
See application file for complete search history.

(56) References Cited

U.S. PATENT DOCUMENTS

| | | |
|---|---|---|
| 2,684,911 A | 7/1954 | Stookey |
| 3,006,775 A | 10/1961 | Chen |
| 3,022,180 A | 2/1962 | Morrissey et al. |
| 3,161,528 A | 12/1964 | Eppler |
| 3,252,778 A | 5/1966 | Goodman et al. |
| 3,804,608 A | 4/1974 | Gaskell et al. |
| 3,816,704 A | 6/1974 | Borom et al. |
| 3,977,857 A | 8/1976 | Mattox |
| 4,155,888 A | 5/1979 | Mooth |
| 4,189,325 A | 2/1980 | Barrett et al. |
| 4,473,653 A | 9/1984 | Rudoi |
| 4,480,044 A | 10/1984 | McAlinn |
| 4,515,634 A | 5/1985 | Wu et al. |
| 5,176,961 A | 1/1993 | Crooker et al. |
| 5,219,799 A | 6/1993 | Beall et al. |
| 5,432,130 A | 7/1995 | Rheinberger et al. |
| 5,507,981 A | 4/1996 | Petticrew |
| 5,618,763 A | 4/1997 | Frank et al. |
| 5,690,819 A | 11/1997 | Chianh |
| 5,698,019 A | 12/1997 | Frank et al. |
| 5,698,482 A * | 12/1997 | Frank et al. .................... 501/10 |
| 5,702,514 A | 12/1997 | Petticrew |
| 5,968,856 A | 10/1999 | Schweiger et al. |
| 6,106,747 A | 8/2000 | Wohlwend |
| 6,121,175 A | 9/2000 | Drescher et al. |
| 6,184,162 B1 | 2/2001 | Speit et al. |
| 6,342,458 B1 | 1/2002 | Schweiger et al. |
| 6,376,397 B1 * | 4/2002 | Petticrew ......................... 501/5 |
| 6,420,288 B2 * | 7/2002 | Schweiger et al. ............... 501/7 |
| 6,455,451 B1 | 9/2002 | Brodkin et al. |
| 6,485,849 B2 | 11/2002 | Petticrew |

(Continued)

FOREIGN PATENT DOCUMENTS

| | | |
|---|---|---|
| CA | 2163792 A1 | 12/1994 |
| CA | 2213390 A1 | 3/1998 |

(Continued)

OTHER PUBLICATIONS

Giassi, L., et al., Injection moulding of LiO2—ZrO2—SiO2—Al2O3 (LZSA) glass ceramics, Glass Technology, vol. 46, No. 3, Jun. 2005, pp. 277-280.

(Continued)

*Primary Examiner* — Noah Wiese

(74) *Attorney, Agent, or Firm* — Ann M. Knab; Thad McMurray

(57) ABSTRACT

The invention relates to a lithium silicate glass ceramic, which contains at least 8.5 wt.-% transition metal oxide selected from the group consisting of oxides of yttrium, oxides of transition metals with an atomic number from 41 to 79 and mixtures of these oxides. The invention also relates to a corresponding lithium silicate glass, a process for the preparation of the glass ceramic and of the glass as well as their use.

24 Claims, No Drawings

(56) References Cited

U.S. PATENT DOCUMENTS

| | | |
|---|---|---|
| 6,514,893 B1 | 2/2003 | Schweiger et al. |
| 6,517,623 B1 | 2/2003 | Brodkin et al. |
| 6,593,257 B1 | 7/2003 | Nagata et al. |
| 6,802,894 B2 | 10/2004 | Brodkin et al. |
| 6,818,573 B2 | 11/2004 | Petticrew |
| 7,316,740 B2 * | 1/2008 | Schweiger et al. ............ 106/35 |
| 7,452,836 B2 | 11/2008 | Apel et al. |
| 7,816,291 B2 | 10/2010 | Schweiger et al. |
| 7,871,948 B2 | 1/2011 | Apel et al. |
| 7,892,995 B2 | 2/2011 | Castillo |
| 8,042,358 B2 | 10/2011 | Schweiger et al. |
| 8,047,021 B2 | 11/2011 | Schweiger et al. |
| 2001/0031446 A1 | 10/2001 | Petticrew |
| 2002/0009600 A1 | 1/2002 | Peng et al. |
| 2002/0010063 A1 | 1/2002 | Schweiger et al. |
| 2002/0031670 A1 | 3/2002 | Goto et al. |
| 2002/0035025 A1 | 3/2002 | Schweiger et al. |
| 2003/0073563 A1 | 4/2003 | Brodkin et al. |
| 2003/0099062 A1 | 5/2003 | Kataoka et al. |
| 2005/0098064 A1 | 5/2005 | Schweiger et al. |
| 2005/0209082 A1 | 9/2005 | Apel et al. |
| 2006/0139091 A1 | 6/2006 | Fratti |
| 2008/0120994 A1 | 5/2008 | Schweiger et al. |
| 2009/0023574 A1 * | 1/2009 | Holand et al. ............... 501/48 |
| 2009/0162608 A1 * | 6/2009 | Yagi et al. ................. 428/141 |
| 2009/0256274 A1 | 10/2009 | Castillo |
| 2009/0258778 A1 | 10/2009 | Castillo |
| 2010/0083706 A1 | 4/2010 | Castillo |
| 2011/0030423 A1 | 2/2011 | Johannes et al. |
| 2011/0256409 A1 * | 10/2011 | Ritzberger et al. .......... 428/432 |
| 2012/0094822 A1 | 4/2012 | Castillo et al. |
| 2012/0148988 A1 | 6/2012 | Castillo et al. |
| 2012/0248642 A1 | 10/2012 | Ritzberger et al. |
| 2012/0309607 A1 | 12/2012 | Durschang et al. |

FOREIGN PATENT DOCUMENTS

| | | |
|---|---|---|
| CA | 2252660 A1 | 5/1999 |
| DE | 2451121 A1 | 5/1975 |
| DE | 19750794 A1 | 6/1999 |
| EP | 0231773 A1 | 8/1987 |
| EP | 0536479 A1 | 4/1993 |
| EP | 0536572 A1 | 4/1993 |
| EP | 0827941 A1 | 3/1998 |
| EP | 0817597 B1 | 9/1999 |
| EP | 0774933 B1 | 12/2000 |
| EP | 1127564 A2 | 8/2001 |
| EP | 1505041 A1 | 2/2005 |
| GB | 752243 A | 7/1956 |
| GB | 2284655 A | 6/1995 |
| JP | 32-5080 | 7/1932 |
| JP | 11-74418 A | 3/1999 |
| JP | 2000-103636 A | 11/2000 |
| JP | 2001-184624 A | 6/2001 |
| JP | 2005-263627 A | 9/2005 |
| JP | 2008-515549 A | 5/2008 |
| JP | 5094017 B2 | 12/2012 |
| WO | 9532678 A2 | 12/1995 |
| WO | 2006/042046 A2 | 4/2006 |
| WO | 2009/126317 A1 | 10/2009 |

OTHER PUBLICATIONS

Apel, E., et al., "Influence of Zr02 on the crystallization and properties of lithium disilicate glass-ceramics derived from multi-component system", Journal of European Ceramic Society, 2007, 27, 1571-1577.

Durschang, Dr. Bernhard, "Report of Results", Fraunhofer Institute for Silicate Research ISC Glass and Mineral Materials, 2015.

McMillan, P.W., et al., "The Structure and Properties of a Lithium Zinc Silicate Glass-Ceramic", Journal of Material Science 1966, I. 269-279.

Deubener, J., et al., "Induction time analysis of nucleation and crystal grown in di- and metasilicate glasses", Journal of Non-Crystalline Solids 1993, 163, 1-12.

Holand, W., et al., "Glass-ceramic technology", American Chemical Society 2002, Westerville OH, USA.

Holand, W., et al., "Control of nucleation in glass ceramics", Phil. Trans. Soc. Lond. A 2003, 361, 575-589.

Holand, W., et al., "Principles and phenomena of bioengineering with glass-ceramics of dental restoration", Journal of the European Ceramics Society 2007, 27, 1571-1577.

Ivoclar Vivadent, Inc., IPS e.max lithium disilicate, 627329, Rev. Feb. 2009.

Borom, M.P., et al., "Strength and Microstructure in Lithium Disilicate Glass Ceramics", J. Am. Ceram. Soc., 1975,58, 385-391.

Von Clausbruch, et al., "Effect of ZnO on the Crystallization, Microstructure, and Properties of Glass-Ceramics in the $SiO_2$—$Li_2O$—$K_2O$—$P_2O_5$ System," Glastech. Ber. Glass Sci. Technol. 74(8):223-229(2001).

Von Clausbruch, et al., "Effect of $P_2O_5$ on the Crystallization and Microstructure of Glass-Ceramics in the $SiO_2$—$Li_2O$—Zn)—$P_2O_5$ System," Glastech. Ber. Glass Sci. Technol. 74(8):223-229(2001).

Stookey, S.D., "Chemical Machining of Photosensitive Glass," Ind. Eng. Chem. 45:115-118 (1993).

Oliveria et al., "Sintering and Crystallization of a GlassPowder in the $Li_2O$—$ZrO_2$—$SiO_2$ System," J. Amer. Ceramic Soc. 81(3):777-780 (1998).

* cited by examiner

LITHIUM SILICATE GLASS CERAMIC AND GLASS WITH TRANSITION METAL OXIDE

CROSS-REFERENCE TO RELATED APPLICATIONS

This application is a continuation application of U.S. Ser. No. 13/079,063, filed Apr. 4, 2011, which claims the benefit of European Patent Application Serial No. 10160222.5, filed Apr. 16, 2010 and European Patent Application Serial No. 10168792.9, filed Jul. 7, 2010, all of which are hereby incorporated by reference in their entirety.

TECHNICAL FIELD

The invention relates to lithium silicate glass ceramics and glasses with a high content of an element with a high atomic number, which are suitable in particular for use as dental materials, for example for the preparation of dental restorations.

BACKGROUND OF THE INVENTION

Lithium silicate glass ceramics are characterized by very good mechanical properties, which is why they have been used for a long time in the dental field and primarily for preparing dental crowns and small bridges. The known lithium silicate glass ceramics usually contain as main components $SiO_2$, $Li_2O$, $Al_2O_3$, alkali metals such as $Na_2O$ or $K_2O$ and nucleating agents such as $P_2O_5$. In addition, they can contain as further components for example further alkali metal oxides and/or alkaline earth metal oxides and/or ZnO. Glass ceramics are also known which contain small quantities of further metal oxides and in particular colouring and fluorescent metal oxides.

EP 1 505 041 and U.S. Pat. No. 7,316,740, which is hereby incorporated by reference in its entirety, describe lithium silicate glass ceramics which can additionally contain 0 to 2 wt.-% $ZrO_2$ as well as 0.5 to 7.5 wt.-% and in particular 0.5 to 3.5 wt.-% colouring and fluorescent metal oxides. EP 1 688 398 and U.S. Pat. No. 7,452,836, which is hereby incorporated by reference in its entirety, describe similar lithium silicate glass ceramics which are substantially free of ZnO and can also contain, in addition to the above-mentioned quantities of colouring and fluorescent metal oxides, 0 to 4 wt.-% $ZrO_2$, wherein however to achieve high strengths smaller quantities of from 0 to 2 wt.-% $ZrO_2$ are preferred. The glass ceramics are processed into the desired dental restorations in particular in the form of lithium metasilicate glass ceramics by means of CAD/CAM methods, wherein a subsequent heat treatment effects the conversion of the metasilicate phase to the high-strength disilicate phase.

U.S. Pat. No. 6,455,451, which is hereby incorporated by reference in its entirety, relates to lithium disilicate glass ceramics which, in addition to other components, can also contain transition metal oxides. It is proposed inter alia, in order to increase the refractive index of the glass matrix, to add small quantities of heavy elements such as Sr, Y, Nb, Cs, Ba, Ta, Ce, Eu or Tb. Thus, for example, $CeO_2$ and $Tb_4O_7$ can be used in quantities of from 0 to 1 wt.-%, $Nb_2O_3$ and $Ta_2O_5$ in quantities of from 0 to 2 wt.-% and $ZrO_2$ and $Y_2O_3$ in quantities of from 0 to 3 wt.-%. In one embodiment, $Ta_2O_5$ is said to be able to be present in a quantity of from 0.5 to 8 wt.-%, even though the specific examples contain at most 2.02 wt.-% of this oxide.

U.S. Pat. Nos. 5,176,961 and 5,219,799, which are hereby incorporated by reference in their entirety, disclose glass ceramics for example for the production of crockery, which can contain as colorants specific transition metal oxides such as $CeO_2$, $Co_3O_4$, $Cr_2O_3$, $CuO$, $Fe_2O_3$, $MnO_2$, $NiO$ and $V_2O_5$ in a quantity of from 0.01 to 7 wt.-%.

U.S. Pat. Nos. 5,507,981 and 5,702,514 which are hereby incorporated by reference in their entirety, describe processes for shaping dental restorations and glass ceramics that can be used in these processes. These are in particular lithium disilicate glass ceramics which can contain 0 to 5 wt.-% colouring oxides such as $SnO_2$, $MnO$, $CeO$, $Fe_2O_3$, $Ni_2O$, $V_2O_3$, $Cr_2O_3$ or $TiO_2$.

Known glass ceramics based on lithium silicate often have optical properties which do not adequately satisfy the aesthetic requirements in particular in connection with the use as dental materials. Thus known glass ceramics often have an unfavourable refractive index. With glass ceramics in particular there is the problem that the refractive indices of the crystalline phase and of the glass phase usually differ markedly from each other, which in most cases results in an undesired clouding of the glass ceramic. Similar problems exist for example in the case of composites because the refractive indices of known glass ceramics and glasses usually differ from those of the polymer phase. There is therefore a need for glass ceramics based on lithium silicate the refractive index of which can be easily varied, but without the other properties being substantially impaired. Moreover, it is desirable that such glass ceramics can be prepared and crystallized under conditions comparable to those for customary glass ceramics.

DETAILED DESCRIPTION OF THE INVENTION

The lithium silicate glass ceramic according to the invention is characterized in that it comprises at least 8.5 wt.-% transition metal oxide selected from the group consisting of oxides of yttrium, oxides of transition metals with an atomic number from 41 to 79 and mixtures of these oxides.

In general it is preferred that the transition metal oxide as component of the glass ceramic according to the invention or of the glass according to the invention effects substantially no colour change compared with a corresponding glass ceramic or a corresponding glass without the addition of this component. In particular, the transition metal oxide is colourless and/or non-fluorescent.

The transition metal oxide is preferably selected from the group consisting of oxides of Y, Nb, La, Ta, W and mixtures of these oxides.

Glass ceramics are preferred which comprise 8.5 to 30.0 wt.-%, preferably 9.0 to 25.0 wt.-%, in particular 9.5 to 20.0 wt.-%, preferred 10.0 to 18.0 wt.-%, more preferred 10.5 to 16.0 wt.-% and most preferred 11.0 to 15.0 wt.-% transition metal oxide selected from one or more of the above-named groups.

Surprisingly, by using the high content according to the invention of transition metal with a high atomic number, the refractive index of glass ceramics and glasses based on lithium silicate can be easily adjusted without other properties being substantially impaired. In particular it was shown unexpectedly that the high content of transition metal with a high atomic number usually neither impedes the desired crystallization of lithium disilicate nor leads to the formation of undesired secondary crystal phases, with the result that glass ceramics with excellent optical and mechanical properties are obtained according to the invention.

A glass ceramic which comprises 54.0 to 80.0 and in particular 60.0 to 70.0 wt.-% $SiO_2$ is further preferred.

In addition, a glass ceramic which comprises 11.0 to 19.0 and in particular 12.0 to 15.0 wt.-% $Li_2O$ is preferred.

It has proven particularly preferable if the glass ceramic comprises 0.5 to 12.0 and in particular 2.5 to 6.0 wt.-% nucleating agents. Preferred nucleating agents are selected from $P_2O_5$, $TiO_2$, metals, e.g. Pt, Pd, Au, Ag, or mixtures thereof. Particularly preferably, the glass ceramic comprises $P_2O_5$ as nucleating agent. Surprisingly, in particular $P_2O_5$ as nucleating agent effects the formation of desired lithium disilicate crystals while largely preventing the formation of undesired secondary crystal phases.

The glass ceramic according to the invention preferably comprises a further alkali metal oxide in an amount of from 0.5 to 13.0, preferably 1.0 to 7.0 and particularly preferably 2.0 to 5.0 wt.-%. The term "further alkali metal oxide" refers to alkali metal oxide with the exception of $Li_2O$. The further alkali metal oxide is in particular $K_2O$, $Cs_2O$ and/or $Rb_2O$ and is particularly preferably $K_2O$. It is assumed that the use of $K_2O$ contributes to the strengthening of the glass network compared with the $Na_2O$ used in conventional glass ceramics. It is preferred that the glass ceramic comprises less than 2.0, in particular less than 1.0, preferably less than 0.5 wt.-% and particularly preferably essentially no $Na_2O$.

It is further preferred that the glass ceramic comprises up to 6.0 wt.-% and in particular 0.1 to 5.0 wt.-% alkaline earth metal oxide, wherein the alkaline earth metal oxide is in particular CaO, BaO, MgO, SrO or a mixture thereof.

It is furthermore preferred that the glass ceramic comprises up to 6.0 wt.-% and in particular 0.1 to 5.0 wt.-% ZnO.

The glass ceramic according to the invention can moreover also comprise additional components which are selected in particular from oxides of trivalent elements, further oxides of tetravalent elements, further oxides of pentavalent elements, melt accelerators, colorants and fluorescent agents.

A glass ceramic which comprises 0.2 to 8.0, in particular 1.0 to 7.0 and preferably 2.5 to 3.5 wt.-% oxide of trivalent elements is preferred, wherein this oxide is selected in particular from $Al_2O_3$, $Bi_2O_3$ and mixtures thereof, and preferably is $Al_2O_3$.

The term "further oxides of tetravalent elements" refers to oxides of tetravalent elements with the exception of $SiO_2$. Examples of further oxides of tetravalent elements are $ZrO_2$, $SnO_2$ and $GeO_2$, and in particular $ZrO_2$.

The term "further oxides of pentavalent elements" refers to oxides of pentavalent elements with the exception of $P_2O_5$. An example of a further oxide of pentavalent elements is $Bi_2O_5$.

A glass ceramic which comprises at least one further oxide of tetravalent elements or one further oxide of pentavalent elements is preferred.

Examples of melt accelerators are fluorides.

Examples of colorants and fluorescent agents are chromophoric or fluorescent oxides of d and f elements, such as the oxides of Sc, Ti, Mn, Fe, Ag, Ce, Pr, Tb, Er and Yb, in particular Ti, Mn, Fe, Ag, Ce, Pr, Tb and Er.

A glass ceramic which comprises at least one and preferably all of the following components is particularly preferred:

| Component | wt.-% |
| --- | --- |
| $SiO_2$ | 54.0 to 80.0, in particular 60.0 to 70.0 |
| $Li_2O$ | 11.0 to 19.0, in particular 12.0 to 15.0 |
| $K_2O$ | 0.5 to 13.5, in particular 1.0 to 7.0 |
| $Al_2O_3$ | 0.2 to 8.0, in particular 1.0 to 7.0 |
| Alkaline earth oxide | 0 to 6.0, in particular 0.1 to 5.0 |
| ZnO | 0 to 6.0, in particular 0.1 to 5.0 |
| Transition metal oxide | 8.5 to 30.0, in particular 9.0 to 25.0 |
| $P_2O_5$ | 0.5 to 12.0, in particular 2.5 to 6.0 |
| $ZrO_2$ | 0.1 to 4.0, in particular 0.5 to 2.0 |
| Colorants and fluorescent agents | 0.1 to 8.0, in particular 0.2 to 2.0. |

The term "main crystal phase" used below refers to the crystal phase which has the highest proportion by volume compared with other crystal phases.

The glass ceramic according to the invention preferably has lithium metasilicate as main crystal phase. In particular the glass ceramic comprises more than 5 vol.-%, preferably more than 10 vol.-% and particularly preferably more than 15 vol.-% of lithium metasilicate crystals, relative to the total glass ceramic.

In a further preferred embodiment, the glass ceramic has lithium disilicate as main crystal phase. In particular the glass ceramic comprises more than 5 vol.-%, preferably more than 10 vol.-% and particularly preferably more than 15 vol.-% of lithium disilicate crystals, relative to the total glass ceramic.

The lithium disilicate glass ceramic according to the invention is characterized by particularly good mechanical properties and can be produced by heat treatment of the lithium metasilicate glass ceramic according to the invention.

It is also surprising that, despite its high content of a transition metal with a high atomic number, the lithium disilicate glass ceramic according to the invention usually has a good translucency and no amorphous-amorphous phase separation occurs in it and it can thus be used for example for the aesthetically pleasing coating of dental restorations.

The lithium disilicate glass ceramic according to the invention has good mechanical properties and a high chemical resistance.

The invention also relates to a lithium silicate glass which comprises the components of the glass ceramic according to the invention described above. In respect of preferred embodiments of this glass, reference is made to the preferred embodiments described above of the glass ceramic according to the invention. It was shown surprisingly that, despite the high content of transition metal with a high atomic number, homogeneous, clear glasses can be obtained which display no undesired phenomena such as amorphous-amorphous phase separation or spontaneous crystallization. These glasses are therefore suitable for the preparation of the glass ceramic according to the invention. Alternatively, a use for example as filler for example in dental materials, in particular inorganic-organic composites, is also possible. A subject of the invention is also a polymerizable composition which comprises a glass ceramic or a glass as described above and at least one polymerizable monomer. Suitable monomers and further constituents of composites are known to a person skilled in the art.

A lithium silicate glass with nuclei which are suitable for the formation of lithium metasilicate and/or lithium disilicate crystals is particularly preferred.

The glass according to the invention with nuclei can be produced by heat treatment of a correspondingly composed starting glass. By a further heat treatment the lithium metasilicate glass ceramic according to the invention can then be formed, which in turn can be converted into the lithium disilicate glass ceramic according to the invention by further heat treatment. The starting glass, the glass with nuclei and the lithium metasilicate glass ceramic can consequently be seen as precursors for the production of the high-strength lithium disilicate glass ceramic.

The glass ceramic according to the invention and the glass according to the invention are present in particular in the form of powders or blanks, as they can easily be further processed in these forms. They can, however, also be present in the form of dental restorations, such as inlays, onlays, crowns or abutments.

The invention also relates to a process for the preparation of the glass ceramic according to the invention and the glass with nuclei according to the invention, in which a starting glass with the components of the glass ceramic or the glass is subjected to at least one heat treatment in the range of from 450 to 950° C.

The starting glass therefore comprises at least 8.5 wt.-% oxide of at least one transition metal as defined above. In addition, it preferably also comprises suitable quantities of $SiO_2$ and $Li_2O$, in order to make possible the formation of a lithium silicate glass ceramic. Furthermore, the starting glass can also contain further components, such as are given above for the lithium silicate glass ceramic according to the invention. Those embodiments are preferred which are also given as preferred for the glass ceramic.

To prepare the starting glass, the procedure is in particular that a mixture of suitable starting materials, such as carbonates, oxides, phosphates and fluorides, is melted at temperatures of in particular from 1300 to 1600° C., preferably 1450 to 1500° C., for 2 to 10 h. To achieve a particularly high homogeneity, the obtained glass melt is poured into water in order to form a glass granulate, and the obtained granulate is then melted again.

The melt can then be poured into moulds to produce blanks of the starting glass, so-called solid glass blanks or monolithic blanks. The cooling preferably takes place from a temperature of 500° C. with a cooling rate of 3 to 5 K/min to room temperature. This is advantageous in particular for the production of stress-free glass products.

It is also possible to put the melt into water again in order to prepare a granulate. This granulate can then be pressed, after grinding and optionally addition of further components, such as colorants and fluorescent agents, to form a blank, a so-called powder green compact.

Finally, the starting glass can also be processed to form a powder after granulation.

The starting glass is then subjected, e.g. in the form of a solid glass blank, a powder green compact or in the form of a powder, to at least one heat treatment in the range of from 450 to 950° C. It is preferred that a first heat treatment is initially carried out at a temperature in the range of from 500 to 600° C. to prepare a glass according to the invention with nuclei which are suitable for forming lithium metasilicate and/or lithium disilicate crystals. This glass can then preferably be subjected to at least one further temperature treatment at a higher temperature and in particular more than 570° C. to effect crystallization of lithium metasilicate or lithium disilicate.

The at least one heat treatment carried out in the process according to the invention can also take place within the framework of the pressing or sintering of the glass according to the invention or the glass ceramic according to the invention onto a ceramic.

Dental restorations, such as inlays, onlays, crowns or abutments, can be prepared from the glass ceramic according to the invention and the glass according to the invention. The invention therefore also relates to their use for the preparation of dental restorations.

In view of the above-described properties of the glass ceramic according to the invention and the glass according to the invention as its precursor, these are also suitable in particular for use in dentistry. A subject of the invention is therefore also the use of the glass ceramic according to the invention or the glass according to the invention as a dental material and in particular for the preparation of dental restorations or as a coating material for dental restorations, such as crowns and bridges.

The invention is described in further detail below with reference to examples.

EXAMPLES

Examples 1 to 10

Composition and Crystal Phases

A total of 10 glasses and glass ceramics with the composition given in Table I (each in wt.-%) were prepared by melting corresponding starting glasses followed by heat treatment for controlled nucleation and crystallization.

The starting glasses were firstly melted in a 100 to 200 g scale from customary raw materials at 1400 to 1500° C. and transformed into glass frits by pouring them into water. These glass frits were then melted a second time at 1450 to 1550° C. for 1 to 3 h for the homogenization. The obtained glass melts were poured into pre-heated moulds to produce glass monoliths. These glass monoliths were transformed into glasses and glass ceramics according to the invention by thermal treatment.

The crystal phases obtained after completion of all heat treatments were determined by high-temperature X-ray diffraction (HT-XRD) at the temperatures listed in each case in Table I. Surprisingly, glass ceramics with lithium disilicate as main crystal phase were always obtained. Despite the high content of transition metals with a high atomic number, no secondary crystal phases were found with these transition metals.

Finally, the refractive indices of the respective glass phases were determined using Abbe refractometry (20° C., 589 nm). It was shown that the glass ceramics according to the invention have a much higher refractive index than a comparison glass ceramic.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

TABLE I

|         | 1    | 2    | 3    | 4    | 5    | 6    | 7    | 8    | 9    | 10   |
|---------|------|------|------|------|------|------|------|------|------|------|
| $SiO_2$ | 67.4 | 58.4 | 66.4 | 63.5 | 67.0 | 61.8 | 66.4 | 66.4 | 61.8 | 54.5 |
| $K_2O$  | 3.7  | 1.0  | 2.9  | 2.8  | 2.9  | 1.0  | 2.9  | 2.9  | 1.0  | 0.5  |
| $Li_2O$ | 14.1 | 12.1 | 13.8 | 13.2 | 14.4 | 13.2 | 13.8 | 13.8 | 13.2 | 11.3 |

TABLE I-continued

|  | 1 | 2 | 3 | 4 | 5 | 6 | 7 | 8 | 9 | 10 |
|---|---|---|---|---|---|---|---|---|---|---|
| $Al_2O_3$ | 3.2 | 1.0 | 2.9 | 2.5 |  | 1.0 | 2.9 | 2.9 | 1.0 | 0.5 |
| $P_2O_5$ | 3.1 | 2.5 | 4.0 | 4.0 | 4.0 | 5.0 | 4.0 | 4.0 | 5.0 | 3.2 |
| $WO_3$ | 8.5 |  |  |  |  |  |  |  |  |  |
| $Nb_2O_5$ |  |  | 10.0 |  |  |  |  |  |  |  |
| $Ta_2O_5$ |  |  |  |  |  |  | 10.0 |  |  |  |
| $La_2O_3$ |  | 25.0 |  |  |  |  |  | 10.0 | 18.0 | 30.0 |
| $Y_2O_3$ |  |  |  | 14.0 | 10.0 | 18.0 |  |  |  |  |
| $CeO_2$ |  |  |  |  | 1.0 |  |  |  |  |  |
| $Er_2O_3$ |  |  |  |  | 0.3 |  |  |  |  |  |
| $Tb_4O_7$ |  |  |  |  | 0.4 |  |  |  |  |  |
| Total | 100.0 | 100.0 | 100.0 | 100.0 | 100.0 | 100.0 | 100.0 | 100.0 | 100.0 | 100.0 |
| Crystal phase(s) HT-XRD | $Li_2Si_2O_5$ $Li_3PO_4$ (800° C.) |  | $Li_2Si_2O_5$ (800°) | $Li_2Si_2O_5$ $KAlSiO_4$ (820°) | $Li_2Si_2O_5$ (780°) | $Li_2Si_2O_5$ $Li_2SiO_3$ (800°) | $Li_2Si_2O_5$ (800°) | $Li_2Si_2O_5$ $Li_2SiO_3$ (700° C.) | $Li_2Si_2O_5$ $LaPO_4$ (800° C.) |  |
| Refractive index $n_d$ | 1.5312 |  | 1.5547 | 1.5553 | 1.5494 | 1.5643 | 1.5403 | 1.5422 | 1.5586 |  |

The invention claimed is:

1. Lithium silicate glass ceramic, which comprises
   at least 8.5 wt.-% transition metal oxide selected from the group consisting of oxides of yttrium, oxides of transition metals with an atomic number from 41 to 79 and mixtures of these oxides,
   at least 2.8 wt.-% $K_2O$, and
   further comprises lithium metasilicate or lithium dis-silicate as main crystal phase.

2. Glass ceramic according to claim 1, which comprises more than 5 vol. % of lithium metasilicate or lithium disilicate crystals.

3. Glass ceramic according to claim 1, which comprises at least 8.5 wt.-% transition metal oxide selected from the group consisting of oxides of Y, Nb, La, Ta, W and mixtures of these oxides.

4. Glass ceramic according to claim 1, which comprises 54.0 to 80.0 wt.-% $SiO_2$.

5. Glass ceramic according to claim 1, which comprises 11.0 to 19.0 wt.-% $Li_2O$.

6. Glass ceramic according to claim 1, which comprises 0.5 to 12.0 wt.-% nucleating agent, wherein the nucleating agent is selected from $P_2O_5$, $TiO_2$, and/or metals.

7. Glass ceramic according to claim 1, which comprises further alkali metal oxide in an amount of from 0.5 to 13.5 wt.-%, wherein the further alkali metal oxide is $K_2O$, $Cs_2O$ and/or $Rb_2O$.

8. Glass ceramic according to claim 1, which comprises up to 6.0 wt.-% alkaline earth metal oxide, wherein the alkaline earth metal oxide is CaO, BaO, MgO and/or SrO, and/or comprises up to 6.0 wt.-% ZnO.

9. Glass ceramic according to claim 1, which comprises 0.2 to 8.0 wt.-% oxide of trivalent elements, wherein the oxide of trivalent elements is $Al_2O_3$ and/or $Bi_2O_3$.

10. Glass ceramic according to claim 1, which comprises at least one further oxide of tetravalent elements or at least one further oxide of pentavalent elements.

11. Glass ceramic according to claim 10, wherein the at least one further oxide of tetravalent elements comprises $ZrO_2$, $SnO_2$ or $GeO_2$.

12. Glass ceramic according to claim 10, wherein the at least one further oxide of pentavalent elements comprises $Bi_2O_5$.

13. Glass ceramic according to claim 1, which comprises at least one of the following components:

| Component | wt.-% |
|---|---|
| $SiO_2$ | 54.0 to 80.0 |
| $Li_2O$ | 11.0 to 19.0 |
| $Al_2O_3$ | 0.2 to 8.0 |
| $K_2O$ | 2.8 to 13.5 |
| Alkaline earth oxide | 0 to 6.0 |
| ZnO | 0 to 6.0 |
| Transition metal oxide | 8.5 to 30.0 |
| $P_2O_5$ | 0.5 to 12.0 |
| $ZrO_2$ | 0.1 to 4.0 |
| Colorant | 0.1 to 8.0 | and fluorescent agent.

14. Glass ceramic according to claim 1, which is present in the form of a powder, a blank or a dental restoration.

15. Glass ceramic according to claim 1, wherein the refractive index is at least 1.53.

16. Lithium silicate glass, which comprises the components of the glass ceramic according to claim 1, and is capable upon heat treatment of forming lithium metasilicate and/or lithium disilicate crystals as main crystal phase.

17. Glass according to claim 16, which is present in the form of a powder, a blank or a dental restoration.

18. Lithium silicate glass which comprises the components of the glass ceramic according to claim 1 and further comprises nuclei which are suitable for forming lithium metasilicate and/or lithium disilicate crystals as main crystal phase.

19. Glass according to claim 18, wherein the refractive index is at least 1.53.

20. Process for the preparation of the glass ceramic according to claim 1, in which a starting glass with the components of the glass ceramic is subjected to at least one heat treatment in the range of from 450 to 950° C.

21. Process of using the glass ceramic according to claim 1, as a dental material, wherein the dental material is used for coating dental restorations, for the preparation of dental restorations or as filler in inorganic-organic composites.

22. Lithium silicate glass ceramic, which comprises at least 8.5 wt.-% transition metal oxide selected from the group consisting of oxides of yttrium, oxides of transition metals with an atomic number from 41 to 56 and 58 to 79 and mixtures of these oxides and further comprises lithium metasilicate and/or lithium disilicate as main crystal phase.

23. Lithium silicate glass, which comprises the components of the glass ceramic according to claim 22, and is capable upon heat treatment of forming lithium metasilicate and/or lithium disilicate crystals as main crystal phase.

24. Lithium silicate glass which comprises the components of the glass ceramic according to claim 22 and further comprises nuclei which are suitable for forming lithium metasilicate and/or lithium disilicate crystals as main crystal phase.

\* \* \* \* \*